United States Patent [19]

Shuffield

[11] Patent Number: 4,471,782

[45] Date of Patent: Sep. 18, 1984

[54] MEDICAL IMPLEMENT FOR USE IN RECTUM AND METHOD FOR INSERTING SAME

[76] Inventor: Luther Shuffield, 4005 Twilight Dr. South, Fort Worth, Tex. 76116

[21] Appl. No.: 429,815

[22] Filed: Sep. 30, 1982

[51] Int. Cl.³ ............................................. A61M 29/00
[52] U.S. Cl. ................................. 128/341; 128/1 R; 128/343; 604/104
[58] Field of Search .................. 128/1 R, 4, 303.11, 128/DIG. 25, 26, 79, 341–343; 604/15–18, 29, 96, 104–106, 278, 327–330, 338–339, 347–348

[56] References Cited

U.S. PATENT DOCUMENTS

| | | | |
|---|---|---|---|
| 2,711,173 | 6/1955 | Seidler | 604/15 |
| 3,331,371 | 7/1967 | Rocchi et al. | 128/DIG. 25 |
| 3,469,575 | 9/1969 | Vass et al. | 604/278 |
| 3,866,601 | 2/1975 | Russell | 128/4 |
| 3,870,048 | 3/1975 | Yoon | 128/4 |

*Primary Examiner*—Lee S. Cohen
*Assistant Examiner*—Steven Falk
*Attorney, Agent, or Firm*—Larson and Taylor

[57] ABSTRACT

A medical implement including a relatively stiff ring which is positionable through a person's anal opening into the rectum, and a method for inserting same. The implement includes, in combination therewith, a rod having a cradle at the distal end thereof onto which the ring is held while the remainder of the ring is held by tension against the side of the rod. The method includes applying the ring to the rod, inserting the ring, while on the rod, into the rectum and then dislodging the ring from the rod. In one embodiment, the medical implement is an elongated tube forming a catheter for removing waste material from the rectum, wherein the ring forms the inner end of the catheter. The rod comprises an insertion rod usable with the catheter for inserting same. Sponges applied to the side of the catheter outside of the anal opening stabilize it in place. In another embodiment, the medical implement is a rectal liquid infusion tube with the ring forming the periphery of a diaphragm attached to the tube to prevent premature egress of the rectal liquid.

16 Claims, 8 Drawing Figures

MEDICAL IMPLEMENT FOR USE IN RECTUM AND METHOD FOR INSERTING SAME

BACKGROUND OF THE INVENTION

This invention relates to medical applications which involve placing of an implement through the anal opening and into the rectum, and in particular it relates to improvements associated with retaining the implement within the rectum.

Various medical implements are utilized with the body in association with the functioning of the rectum. One such implement is a catheter for removing waste material from the rectum. Another implement is the enema infusion tube which is inserted into the anal opening for the purpose of introducing into the rectum suitable liquids such as enema liquid or barium, the latter for x-ray examination purposes. If it is desired to provide a means for positively retaining the distal end of these medical implements in the rectum, the most common technique is to utilize an inflatable balloon in the vicinity of that distal end. With the balloon deflated the medical implement is introduced through the anal opening. Then, after the balloon and the distal end are inside the rectum, the balloon is inflated so as to prevent removal thereof while carrying out the relevant medical procedure.

However, balloons of this type have a distinct disadvantage. Obviously, the balloon is not visible to the medical operator. Hence, inflating of the balloon will often involve an element of guess work. An over inflated balloon can cause severe damage including rupturing of the rectum wall which, because of infection, can result in death. If the balloon is under inflated, then it will not carry out its function of holding the medical implement within the rectum and concurrently preventing leakage of liquid around the outside of the balloon and through the anal opening.

Certain medical implements are also known wherein means other than an inflatable balloon are utilized for holding the medical implement within the rectum. For example, in the Ronnquist U.S. Pat. No. 4,030,500, a resilient ring is used at the distal end of a catheter. However, this arrangement has the disadvantage that there is no convenient technique for inserting the ring into the rectum.

In the Vass et al U.S. Pat. No. 3,469,575, there is shown an arrangement for introducing liquid into the rectum, which arrangement includes a disk element which is located on the distal, or inner, side of the anal opening. However, this arrangement also has the disadvantage that it lacks a simplified comfortable technique for introducing the same into the rectum.

Hence, there exists a need for medical implements of the type having portions retained within the rectum, which include retaining elements which are comfortable on the subject person and also which may be conveniently, comfortably but efficiently introduced into the person's rectum through the anal opening.

SUMMARY OF THE INVENTION

Hence, it is a purpose of the present invention to provide a new and improved medical implement of the type retained within a person's rectum, and in combination therewith a new and improved technique for conveniently and comfortably introducing the implement through the anal opening into the person's rectum.

This purpose is achieved by providing a medical implement, and a method for inserting same, which includes a stiff, although slightly yielding resilient ring adapted to be positioned in the rectum on the inner side of the anal opening during the relevant medical procedure. In combination therewith, there is provided a convenient and comfortable technique for introducing this ring. This technique involves placing one portion on the ring in a cradle located at the distal end of a rod and retaining the remainder of the ring under tension against the side of the rod. With the ring thus positioned, the rod is easily slid up through the anal opening, after which the ring is dislodged from the rod and permitted to move under its own resilience to assume a transverse position across the rectum.

In one embodiment, the medical implement is a catheter having a stiff ring at the distal end thereof surrounding the distal end opening of the catheter. The catheter itself is an extremely thin walled sheath which extends down through and out of the anal opening whereat it is attached to a conventional collection device. Sponges may be attached to this catheter which exert a force against the outside of the anal opening to stabilize the catheter in place.

To insert this catheter, there is provided for use therewith a suitable insertion rod which is elongated and has a cradle at one end thereof. The ring of the catheter is placed in the cradle with the remainder lying against the side of the insertion rod. A string attached to the ring is pulled to place the ring under tension as the rod is moved up through the anal opening. After this movement of the rod through the anal opening with the ring thereon, the ring is removed, leaving the ring in place with the remainder of the catheter extending out through the anal opening. Preferably the rod has an enlarged proximal end. After the ring is inserted, the rod may be reversed to urge the enlarged end up though the catheter, whereby the thin walled catheter is pulled down over the enlarged end of the rod to stabilize the ring. At this time suitable sponges or the like may be applied to the catheter, after which the rod would be removed and the catheter attached to the collection device.

In another embodiment, the principles of the present invention may be applied to a liquid infusion device of the type intended for introducing a liquid into the rectum. Such liquid may be either enema liquid or barium used for diagnostic purposes. In this embodiment, the elongated infusion tube with the exit openings near the distal end thereof may include a thin membrane diaphragm attached to the tube with the outer periphery thereof formed of the relatively stiff ring. This diaphragm serves the same purpose as the balloons known heretofor in that it prevents premature escape of the liquid.

In accordance with the present invention, the technique for introducing this diaphragm surrounded by the ring comprises placing one portion of the diaphragm in a cradle formed at the distal end of the tube while positioning the remainder of the ring against the tube. After the tube has been moved through the anal opening sufficiently for the ring to be located in the rectum, the diaphragm ring is dislodged from the cradle, whereby it assumes a transverse position across the rectum.

Hence, it is an object of the present invention to provide a new and improved medical implement of the type adapted to be retained within the rectum.

It is still another object of this invention to provide a new and improved method for introducing into the rectum an implement of the type adapted to be retained therein.

It is still another object of this invention to provide a new and improved rectal catheter having a stiff ring at the distal end thereof, together with a new and improved technique for inserting the same.

It is still another object of this invention to provide a new and improved device for introducing liquid into the rectum, which device includes a diaphragm surrounded by a stiff ring preventing premature discharge of the liquid, which infusion tube includes means for conveniently inserting the ring into the rectum.

These and other objects of the present invention will become apparent from the detailed description to follow, together with the accompanying drawings.

BRIEF DESCRIPTION OF THE DRAWINGS

There follows a detailed description of the preferred embodiments of the invention, which description is to be read together with the accompanying drawings wherein.

DETAILED DESCRIPTION OF THE PREFERRED EMBODIMENTS

Figure 1:
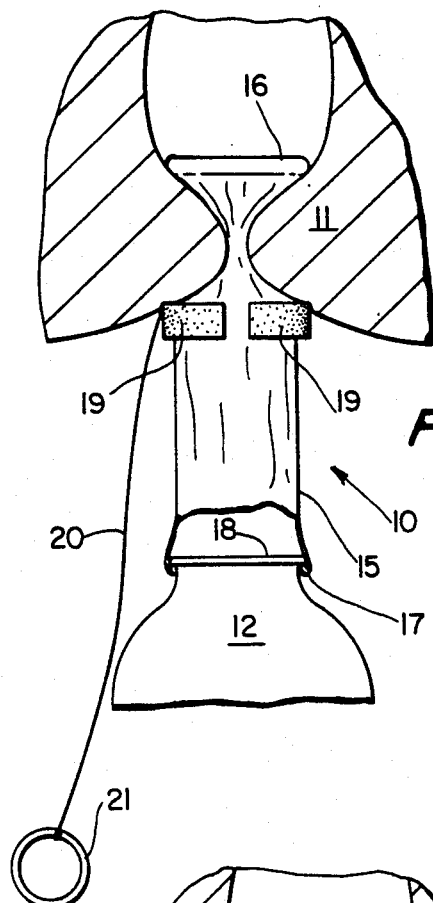
FIG. 1 is a side elevational view of a rectal catheter of the present invention, shown in position relative to a person's anal opening and rectum, in normal use connected to a conventional collection receptacle.

Referring now to the drawings, like elements are represented by like numerals throughout the several views.

Referring to FIG. 1, there is shown a rectal catheter 10 positioned to pass through the anal opening formed between the anal sphincter muscles 11. A conventional enema collection bag 12 is attached to the lower end of catheter 10. This catheter includes a relatively stiff, although slightly yielding ring 16 forming the distal end thereof. This ring may be made for example out of yieldable plastic or hard rubber. Attached to this ring and extending downwardly therefrom is a very thin walled sheath 15. The combination of ring 16 with sheath 15 has the advantage that when the catheter is not in use, the anal sphincter muscles 11 may completely relax since the element passing therethrough, the thin walled sheath 15, takes up virtually no room in the collapsed condition.

At its lower end, the catheter 10 includes a bead 17 adapted to fit snugly on a flange 18 of the collection bag 12. Suitable sponges 19 may be attached to the outer surface of sheath 15, preferably completely surrounding same, to exert a force against the outer side of the anal opening for retaining the ring 16 stabilized in place. A cord 21 attached to the ring 16 passes through the anal opening to a convenient handle 21. This of course provides for easy removal of the ring 16, and hence also the entire catheter 10, after completion of its use.

Figure 2:
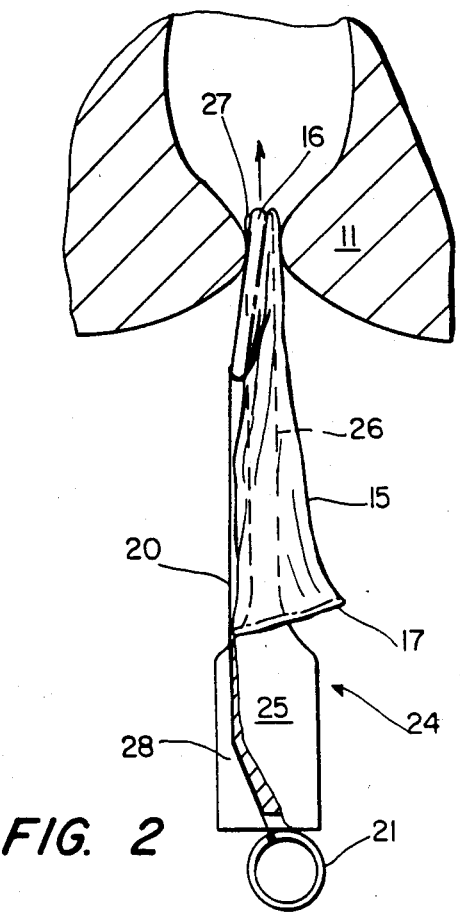
FIG. 2 is a side elevational view similar to FIG. 1 but showing a first step in the introduction of the rectal catheter through the anal opening.
Figure 3:
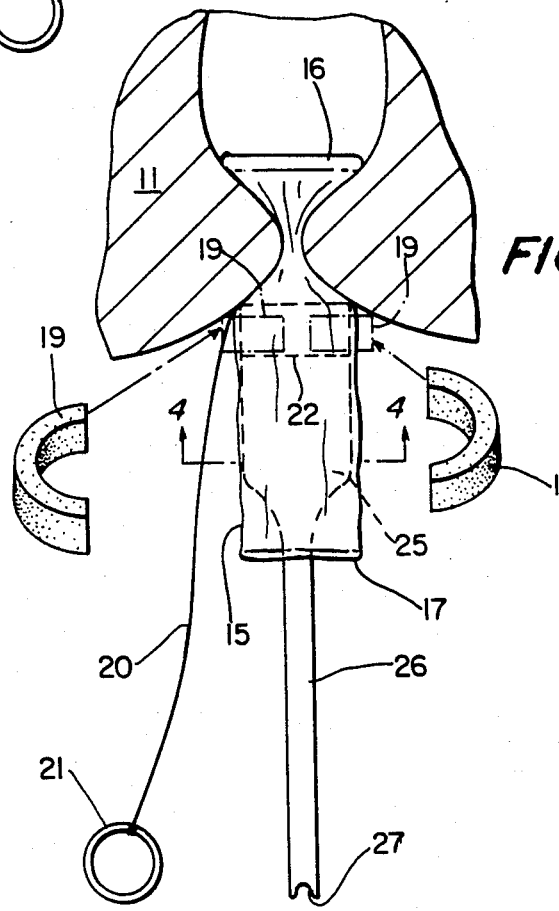
FIG. 3 is a side elevational view similar to FIG. 2 but showing subsequent stages in the introduction of the rectal catheter.

The method for inserting the catheter 10 is illustrated in FIGS. 2 and 3. Referring to FIG. 2, there is provided an inserter 24 having a large end 25 and a small end 26, the latter including a cradle 27 at the distal end thereof. As shown in FIG. 2, one portion of the ring 16 lies in this cradle while the remainder of the ring lies against the side of the inserter 24. The ring is so arranged that the portion connected to cord 20 is at the lower most end. The cord 20 is placed under tension. Preferably (and referring also to FIG. 4) the cord may be placed through a slot 28 in the enlarged end 25 of the inserter and the handle 21 located against the bottom of the inserter. This holds the ring 16 under tension. With the elements thus arranged, the inserter 24 is moved up through the anal opening to carry the ring 16 up into the rectum as shown by the arrows in FIG. 2.

Figure 4:
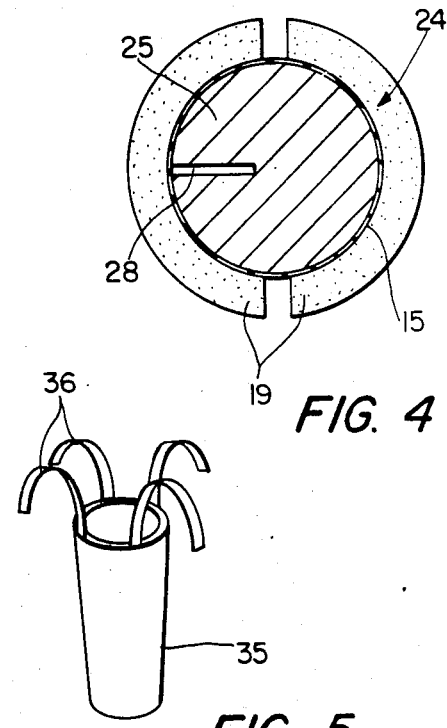
FIG. 4 is a cross-sectional view taken along line 4—4 of FIG. 3.

Referring to FIG. 3, after the ring 16 has been located in the rectum, the handle 21 is moved sideways out of slot 28 and the inserter 24 is removed, leaving the ring 16 in the rectum, free to position itself thereacross. The inserter 24 is then reversed so that the large end thereof is placed up through the proximal end of the catheter and up against the outer end of the anal opening. This position is shown in FIG. 3. With the inserter 24 thus positioned, the sheath 15 can be stretched downwardly, supported by the inserter 24. At this time suitable sponges, for example, semicircular sponges 19 having adhesive on the inner circles thereof may be placed against the outer surface of the sheath 15 as the latter is supported by the large end 25 of the inserter. A score line 22 may be provided on the inserter or the sheath to assist in locating the sponges 19. The inserter, the sheath 15 and the sponges are illustrated in FIG. 4.

Figure 5:
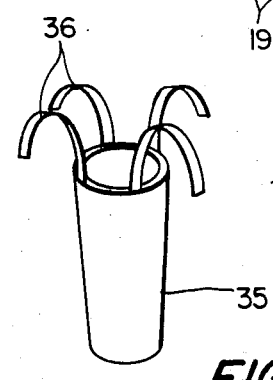
FIG. 5 shows an accessory for facilitating attachment of the rectal catheter to a conventional collection receptacle.

FIG. 5 illustrates a special accessory which may assist in seating the ring 16. The element 35 which is shaped like a hollow thimble with resilient arms 36 may be placed over the end 27 of the inserter 24 such that the arms 36 engage against the bottom of sheath 15, against the bead 17, to help pull the same downwardly to position the ring 16.

Figure 6:
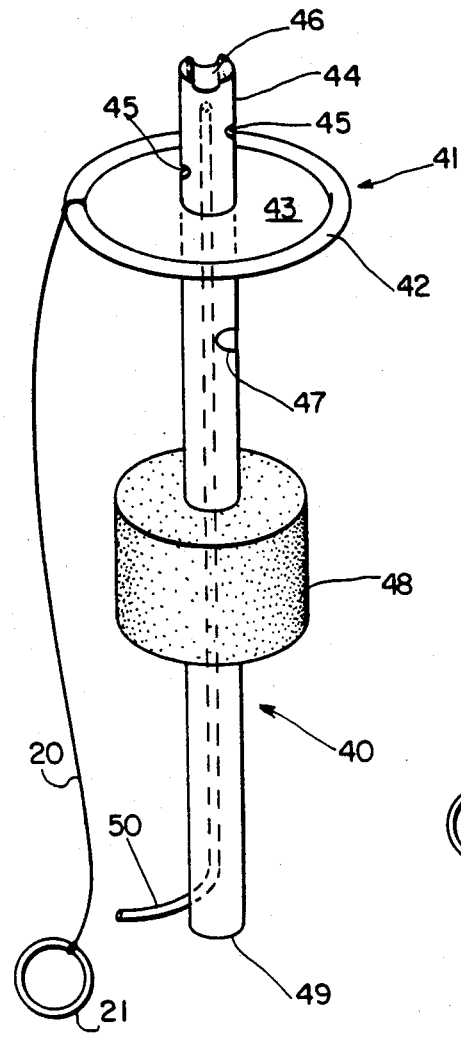
FIG. 6 is a perspective view of another embodiment of the invention, namely a liquid infusion tube which includes features of the present invention.
Figure 7:
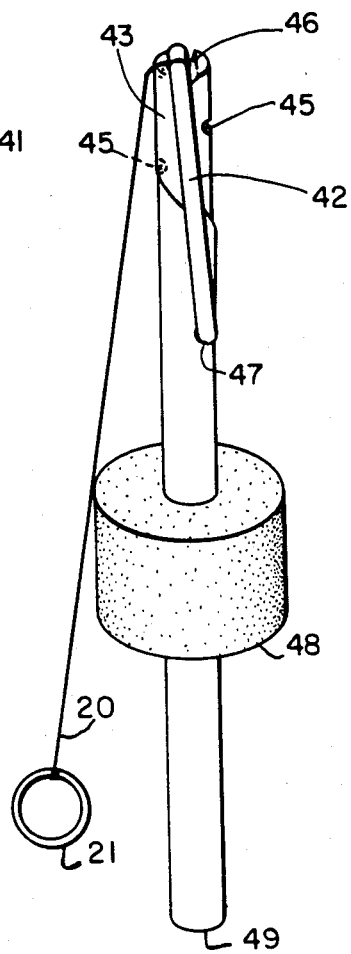
FIG. 7 is a side elevation of the tube of FIG. 6, but with the diaphragm and ring positioned on the tube ready for insertion through the anal opening.
Figure 8:
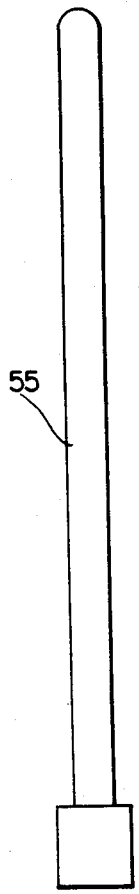
FIG. 8 is a side elevational view of a stylus adapted for use with the embodiment of FIGS. 6 and 7.

FIGS. 6 through 8 illustrate still another embodiment of the invention. This embodiment of the medical implement, which employs the features of the present invention, comprises an enema infusion tube 40 having a diaphragm 41 thereon. The diaphragm includes a thin inner membrane 43 and an outer stiff seating ring 42. The delivery end of the tube includes liquid outlet openings 45 and a cradle 46. A slot 47 is cut into the tube beneath the diaphragm. Preferably this slot includes a membrane completely covering same, conforming to the curved outer contour of the tube 40. A sponge 48 on the tube 40 is provided for exerting a force against the outside of the anal opening to retain the diaphragm in place. This sponge may be slid along the tube 40. The tube includes at its proximal end 49 an adapter enabling it to be attached to any suitable tube for introducing liquid. An air tube 50 is provided for introducing air up through the tube 40 to enable the doctor to perform double contrast enema using both barium and air.

Referring to FIG. 7, in order to introduce the tube 40 and its diaphragm into the rectum, the diaphragm, which is integral with the tube is turned to pivot about its connection with the tube such that one end thereof rests in the cradle 46. The opposite end thereof is pushed into the cutout 47. So long as no pressure exists within the tube, the ring will rest within the cutout 47. With the elements as shown in FIG. 7, the tube 40 is moved through the anal opening to carry the distal end of the tube and also the ring up into the rectum. If desired, the stylus 55 may be used to dislodge the ring from the cradle 46 and cutout 47 by introducing this stylus through the opening 49 to push the ring out of cutout 47. However, this may be accomplished even more easily by simply attaching the end 49 to the tube for introducing the liquid. The introduced liquid, being under a pressure, would push the membrane covering cutout 47 outwardly to dislodge the lower end of the ring 42 from cutout 47. With this accomplished, the upper end of ring 42 would come out of cradle 46 and assume its transverse positon within the rectum. Additionally, the removal cord 20 and 21 may be used to assist in dislodging the ring 42 from the cradle 46.

The method of operation of the invention, i.e., the method for inserting and utilizing the medical implements described herein have been described already in the description of the individual embodiments. To briefly summarize, according to the method of inserting the medical implements shown and described herein, a portion of diaphragm 16 or 42 is positioned on a rod in the cradle at the distal end of the rod and held in tension against the side of the rod. In this position, the rod is inserted after which the ring is dislodged to assume its appropriate transverse position within the rectum. The medical implements are then utilized in the manner as described above. At the completion of use, the implements are removed. In the case of the catheter, it is removed by simply pulling the cord 20 by means of handle 21. In the case of the liquid infusion tube, it is removed by simply removing the tube itself.

Although the invention has been described in considerable detail with respect to preferred embodiments thereof, it will be apparent that the invention is capable of numerous modifications and variations apparent to those skilled in the art, without departing from the spirit and scope of the invention.

I claim:

1. A method of inserting into a persons anal opening a medical implement having a relatively stiff ring which, in use, is positioned against the inside of the anus, said method comprising the steps of:
   positioning a portion of the ring on the end of an elongated rod such that said portion lies in a cradle formed on the distal end of the rod with the remainder of the ring held under tension against the side of the rod,
   with the ring thus positioned, inserting the rod through the anal opening to carry the ring past the anal sphincter muscles,
   and dislodging the said portion from the cradle so that it is free to position itself transversely across the rectum.

2. The method of claim 1, wherein the medical implement is a rectal catheter for removing waste material through the anus into a suitable container, the ring being a stiff ring forming the distal end of the catheter,
   said step of positioning said portion of the ring comprising placing said portion into the cradle of an insertion rod and applying a tension to the ring across from that portion in the cradle to urge the ring along the side of the insertion rod,
   and the dislodging step comprising releasing said tension on the ring and then removing the rod from the anal opening.

3. The method of claim 2, including a cord attached to the ring, and said step of applying tension comprising attaching the cord to the proximal end of the insertion rod which is that end remote from the cradle.

4. The method of claim 3, further including the step of applying sponges onto the outside of the catheter, outside of the anal opening, to stabilize the catheter in position.

5. The method of claim 2, the end of the rod opposite from the cradle being enlarged, and including, after the insertion rod has been removed, reversing the insertion rod and inserting the large opposite end into the catheter to expand the catheter thereover.

6. The method of claim 5, including the step of applying sponges onto the outside of the catheter, while the large end of the insertion rod is located therein, to stabilize the catheter in its position.

7. The method of claim 1, said rod being a rectal liquid infusion tube with said cradle formed on the distal end of the tube and with the ring formed as the periphery of a diaphragm attached to the tube,
   said step of positioning said portion of the ring comprising placing said portion onto said cradle formed on the distal end of the tube, while retaining the remainder of the ring against the tube,
   and the dislodging step comprising dislodging the ring from the cradle while the infusion tube is in place within the rectum.

8. The method of claim 7, the step of retaining the ring against the tube comprising positioning the end of the ring remote from the cradle into a cutout formed into the tube.

9. The method of claim 8, wherein the cutout is covered by a thin membrane, and said step of retaining the ring comprises pushing back the membrane, and said dislodging step comprises having the pressure of the incoming enema liquid push out the said membrane to push the ring out of the cutout.

10. In combination:
    a medical implement having a relatively stiff ring which, in use, is located in the rectum against the inside of the anus,
    a rod having at its distal end a recessed cradle receiving a portion of the ring and carrying it into and through the anal opening, into the rectum,
    means for applying tension to the ring to position it alongside the rod, under tension, for inserting the ring into the anal opening,
    and means for releasing the tension to dislodge said portion of the ring from the cradle so that the ring is free to position itself transversely across the rectum.

11. The combination of claim 10, wherein the medical implement is a rectal catheter for removing waste material through the anus into a suitable container, the ring being a stiff ring forming the distal end of the catheter,
    and the rod being an insertion rod with the cradle at a distal end thereof, and the means for applying tension comprising a cord attached to the ring which, when stretched, applies the tension.

12. The combination of claim 11, the insertion rod including means for holding the cord to apply the tension.

13. The combination of claim 11, the insertion rod having an enlarged end opposite from the end with the cradle, said enlarged end being of a size to fit up into the catheter to stabilize and stretch it out after the ring is located in the rectum.

14. The combination of claim 13, including a hook means insertable over the insertion rod to engage the proximal end of the catheter to stretch out the catheter.

15. The combination of claim 10, said rod being a rectal liquid infusion tube with said cradle formed on the distal end of the tube and with the ring formed as the periphery of a diaphragm attached to the tube.

16. The combination of claim 15, said tube including a cutout formed in the side thereof, said cutout being covered by a thin membrane, said cutout receiving therein a portion of the ring opposite from the portion in the cradle to thereby place the ring under tension, the membrane being subjected to pressure within the tube such that the pressure of the incoming rectal liquid will urge the ring out of the cutout to thereby assist in dislodging the ring from the cutout and the cradle.

* * * * *